United States Patent [19]
White et al.
[11] Patent Number: 4,922,045
[45] Date of Patent: May 1, 1990

[54] DIESEL LUBRICATING OIL CONSUMPTION CONTROL ADDITIVES

[75] Inventors: William R. White, Wappingers Falls; Mary A. Dahlstrom, Hopewell Junction; Scott O. Lindholm, Newburgh, all of N.Y.

[73] Assignee: Texaco Inc., White Plains, N.Y.

[21] Appl. No.: 81,268

[22] Filed: Aug. 3, 1987

[51] Int. Cl.$^5$ .................................. C07C 7/20
[52] U.S. Cl. .................................. 585/10; 585/2; 585/3; 585/4; 585/11; 585/12; 585/18; 585/19
[58] Field of Search .................. 585/2, 3, 4, 11, 12, 585/18, 19, 10

[56] References Cited

U.S. PATENT DOCUMENTS

| | | | |
|---|---|---|---|
| 3,076,791 | 2/1963 | Hollyday | 585/4 |
| 3,607,749 | 9/1971 | Forbes | 585/3 |
| 3,725,279 | 4/1973 | Armstrong | 585/4 |
| 3,729,415 | 4/1973 | Davis et al. | 585/2 |
| 3,772,169 | 11/1973 | Small et al. | 585/3 |
| 3,772,196 | 11/1973 | St. Clair et al. | 585/3 |
| 3,838,049 | 9/1974 | Souillard et al. | 585/2 |

FOREIGN PATENT DOCUMENTS

| | | | |
|---|---|---|---|
| 573745 | 4/1959 | Canada | 585/10 |
| 1053440 | 1/1967 | United Kingdom | 585/2 |

*Primary Examiner*—Asok Pal
*Attorney, Agent, or Firm*—Robert A. Kulason; James J. O'Loughlin; Vincent A. Mallare

[57] ABSTRACT

An oil consumption controlling additive for heavy duty diesel engines comprising a polymer.

6 Claims, 2 Drawing Sheets

DIESEL LUBRICATING OIL CONSUMPTION CONTROL ADDITIVES

FIELD OF THE INVENTION

This invention relates to diesel lubricating oils and, more particularly, to diesel lubricating oils containing an additive which controls oil consumption.

Currently, most manufacturers of heavy-duty diesel equipment do not recommend single-grade oils for use in their engines in over-the-road service because of high oil consumption. High oil consumption in these engines is thought to be due to wear and/or deposit buildup in the ring-belt region of the piston; it is undesirable for two reasons: more oil is needed during the lifetime of the engine and oil consumption above a certain level may indicate impending engine failure necessitating engine overhaul.

While the typical life of such diesel engines between overhauls is 300,000 miles, major diesel original equipment manufacturers would like to see this interval increased to as much as 500,000–800,000 miles, thereby reducing by half the cost of overhauls on a per-mile basis.

Recent engine test results suggest a means whereby oil consumption of single grade diesel engine oils may be reduced or controlled.

Thus, it is an object of this invention to provide a means for controlling and reducing oil consumption in heavy-duty diesel engines.

Another object is to provide a means for using single-grade oils with a low oil consumption in heavy-duty diesel engines.

As described below, the present additives make it possible to obtain these objects.

SUMMARY OF THE INVENTION

This invention provides an oil consumption control additive for heavy-duty engine lubricating oil compositions. The heavy-duty diesel lubricating oil composition comprises:

(a) a major portion of heavy-duty diesel engine lubricating oil and (b) a minor portion of, as an oil consumption controlling additive, a polymer dissolved in a diluent oil.

The polymers which may be used as the additive are those which can be dissolved in a mineral oil, such as carbon-carbon polymers, copolymers and graft copolymers.

DETAILED DESCRIPTION OF THE INVENTION

The lubricating oil of the present invention is intended to be used in heavy-duty diesel engines as used in tractor trailer trucks in over-the-road service.

Usually, multi-grade oils are preferred in these heavy-duty diesel engines. However, according to the present invention, single-grade oils can be used in these heavy-duty diesel engines as long as they contain the additives of the present invention.

The present heavy-duty diesel engine lubricating oil composition contains (a) the heavy-duty diesel engine lubricating oil as a major portion and (b) the remaining minor portion is a polymer which is an oil consumption controlling additive in a diluent oil.

The polymers which may be used as the oil consumption controlling additive include polymers which traditionally have been used as viscosity index improvers. These polymers are typical carbon-carbon backbone polymers prepared from monomers bearing an ethylenically unsaturated polymerizable double bond and include homopolymers or copolymers prepared from a monomer

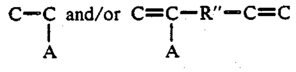

where A may be: hydrogen; a hydrocarbon such as alkyl, aryl, etc.; phenyl; an acetate or less preferred acyloxy (typified by —COOR); halide, etc. R″ may be divalent hydrocarbon typified by alkylene, alkarylene, aralkylene, cycloalkylene, arylene, etc. Examples of the above monomers include acrylates, methacrylates, vinyl halide (such as vinyl chloride), styrene, olefins such as butadiene, isoprene, hexadiene, ethylidene norbornene, etc. Homopolymers of olefins (such as polyethylene, polypropylene, polybutylene, etc.), dienes (such as hydrogenated polyisoprene), or copolymers of ethylene with e.g., butylene and higher olefins, styrene with isoprene and/or butadiene may be employed. The preferred carbon-carbon backbone polymers include those selected from the group consisting of ethylene-propylene copolymers (EPM or EPR) and ethylene-propylene diene third monomer terpolymers (EPDM or EPT). The molecular weight, $\overline{M}n$, of the polymers may be about 10,000 to about 450,000.

In the case of where copolymers are used as the heavy-duty diesel engine lubricating oil consumption controlling additive, monomers may be grafted onto the copolymer but are not necessary to the performance of the additive. The graft monomers which may be used include vinyl or alkyl compounds containing nitrogen (i.e., amides, imides, amines) such as N-vinylpyrrolidone, N-vinyl imidazole, alkyl amine, N-vinyl pyridine, etc.

The oil consumption controlling additives are generally placed in a diluent oil and then incorporated with the heavy-duty diesel engine lubricating oil. The diluents which may be used are generally highly refined low viscosity (typically 50–120 SUS at 100° F.) naphthenic or paraffinic mineral oils such as solvent neutral or pale oils.

The amount of heavy-duty diesel engine lubricating oil consumption controlling additive present in the lubricating oil is from about 0.02 to about 3.0 wt.%.

According to the present invention, the additive as described herein may be initially blended in with the heavy-duty diesel engine lubricating oil which is placed in the diesel engine crankcase. Also, the present additive may be added to the lubricating oil when it has been used to lubricate the diesel engine and associated parts.

The present additive is very effective in controlling the oil consumption in heavy-duty diesel engines either if it is included in the heavy-duty diesel engine lubricating oil at the time the oil is formulated or if it is added to the formulated oil after some use in an engine. This is shown by the comparison of an oil without any additive and the same oil with the present additive. Also, the effect of incorporating the present additive in an oil is compared with the same oil, plain, i.e., without an additive. The comparison is clearly illustrated in the drawings which are described below.

To illustrate the advantages of using the present additives in the lubricating oil of heavy-duty diesel engines, the following Example is provided.

EXAMPLE

To establish the effectiveness of the present oil consumption controlling additive, tests using lubricating oils A–E (Table 1) were made in the Cummins NTC-400 engine, a 6-cylinder, 400-HP, 855 cu.in. engine typical of heavy-duty diesel engines used in over-the-road service. The test procedure employed is particularly relevant because it has recently been included as a requirement in a new American Petroleum Institute oil quality specification, designated CE, for heavy-duty diesel engine oils. The NTC-400 test method was developed by the Cummins Engine Company to simulate oil consumption, deposit accumulation and component wear typical of field service.

The test is conducted in a Cummins Big Cam II engine which has been modified to provide control of elevated operating conditions in the areas of fuel flow, power output, intake manifold air and oil gallery temperatures. These parameters are maintained at extremes not usually encountered in normal operation. The severe operating conditions of this procedure are necessary to acquire significant results within a reasonable time-frame.

The engine is rebuilt prior to each test with new pistons, rings, cylinder liners, intake and exhaust valves, guides and seats. After an oil flush and short break-in sequence, the engine is operated at steady-state conditions, 5 percent overfueled for 200 hours with no oil changes. Oil additions are made every 20 hours at which time the 20-hour average oil consumption value is determined. At the conclusion of the test the engine is disassembled and evaluated for deposits and wear.

The oils used in these tests are shown below in Table I.

TABLE I

| | | Experiment 1 |
|---|---|---|
| Oil | Kinematic Viscosity cSt, 100° C. | Description |
| A | 11.49 | SAE 30 grade diesel engine oil with standard dispersant-inhibitor system |
| B | 19.92 | Oil A plus 9.1% of a solution of polymer in diluent oil |
| C | 18.75 | SAE 50 grade diesel engine oil with standard dispersant-inhibitor system |

Figure 1:
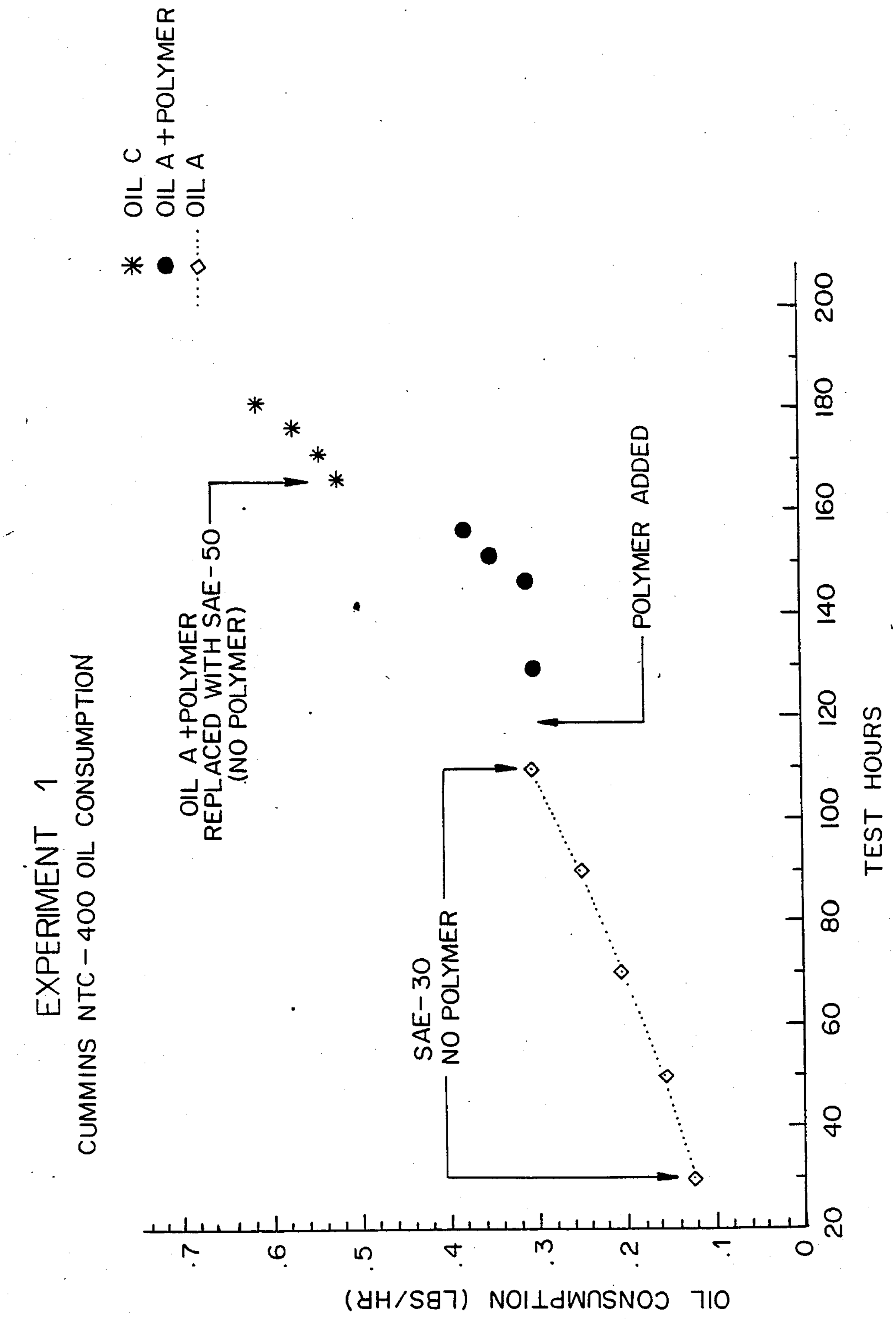
FIG. 1 is a graph illustrating the effect on oil consumption of the present additive when it is added to a standard heavy-duty diesel oil during a test run in a heavy-duty diesel engine.

At the start of Experiment 1, an NTC-400 engine was charged with 69–70 pounds of Oil A, a standard SAE 30 diesel engine oil containing no polymer. As seen in FIG. 1, oil consumption increased steadily from the start of test through 120 hours with use of this oil. At 120 hours, the engine was stopped. Total oil charge was 62 pounds of Oil A. To approximately 2–3 gallons of Oil A drained from the engine, 7 pounds of a solution of polymer in diluent oil were added. This polymer/oil blend was then returned to the engine, resulting in a 9–10 percent dose of polymer solution in the oil and a full oil charge of 69 pounds in the engine. Resulting kinematic viscosity of this polymer-improved oil was 20.71 cSt at 100° C. As can be seen in FIG. 1, oil consumption increase was stopped instantly when this solution of polymer in diluent oil was added to a fully-formulated single grade oil during an on-going engine test. At 160 hours into Experiment 1, the engine was stopped, the polymer/oil blend was drained and the engine was charged with a heavier single-grade oil, Oil C. Oil consumption increased instantly, returning to its original rate of increase. This experiment demonstrates: (a) that the reduction in oil consumption is directly related to the polymer, (b) that the reduction in oil consumption is not related to the viscosity increase which accrued by addition of the polymer and (c) that small amounts of polymer can be used as an after-market control agent to reduce oil consumption.

| | | Experiment 2 |
|---|---|---|
| Oil | Kinematic Viscosity cSt, 100° C. | Description |
| A | 11.49 | See Experiment 1 |
| D | 11.10 | SAE 30 grade diesel engine oil formulated with 3% of a solution of polymer in diluent oil |
| E | 11.31 | Re-blend of Oil A |

In Experiment 2, it was found that oil conumption in the NTC-400 test was controlled when a single-grade oil formulated with a small amount of polymer (Oil D) was used in this engine as compared to single-grade oil(s) formulated without polymer (Oils A and E). The oil consumption results for these formulations in the Cummins NTC-400 test are shown in FIG. 2 along with the API-CE limit for oil consumption as defined by this test.

Figure 2:
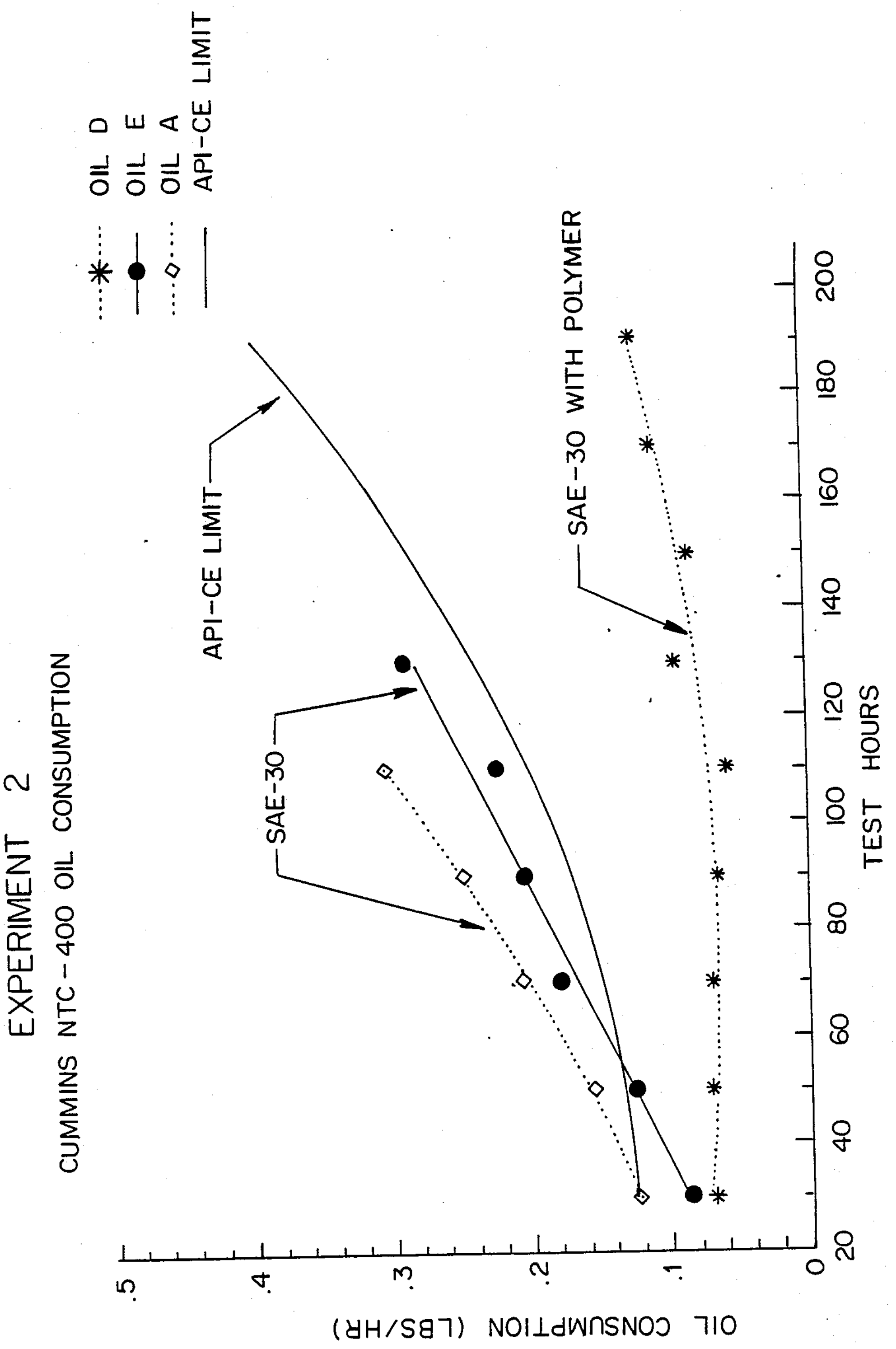
FIG. 2 is a graph comparing the use of the present additive in a standard heavy-duty diesel engine oil to a standard heavy-duty diesel engine oil without the present additive in a diesel engine.

To demonstrate CE quality, which is the highest quality for this type of oil, the curve drawn through the individual oil consumption determinations of an NTC-400 test for a formulation must remain below (low oil consumption) the API-CE limit curve; as shown in FIG. 2, Oils A and E, essentially reblends of the same standard SAE 30 grade diesel engine oil, did not meet this limit. Oil D, which is equivalent to Oils A and E except for the inclusion of polymer, easily meets the API-CE oil consumption limit criterion defined by this test. These data reaffirm the relationship between the polymer and oil consumption control.

We claim:

1. A heavy duty diesel engine lubricating oil composition comprising:

(a) a major portion of a single-grade SAE30 oil or SAE50 oil, heavy duty diesel engine lubricating oil and (b) a minor portion of, as an oil consumption controlling additive, a polymer dissolved in a diluent oil, said polymer being selected from the group consisting of polyethylene, polypropylene, polybutylene, polyisoprene, ethylene-propylene copolymer, polymethyacrylate, ethylene-butylene copolymer, styrene-isoprene copolymer, ethylene-propylene diene third monomer, ethylene-propylene terpolymer and styrene-butadiene copolymer, and wherein monomers are grafted onto said copolymers, said monomers being selected from the group consisting of N-vinylpyrrolidone, N-vinyl imidazole, an alkyl amine, an alkyl amide, an alkyl imide and N-vinyl pyridine.

2. The heavy-duty diesel engine lubricating oil composition of claim 1, wherein the amount of said additive present in the lubricating oil is from about 0.02 to about 3.0 wt.%.

3. The heavy-duty diesel engine lubricating oil composition of claim 1, wherein the oil consumption meets the API-CE limit in the Cummins NTC-400 test.

4. The lubricating oil composition of claim 1, wherein the polymer has molecular weight of about 10,000 to about 450,000.

5. The lubricating oil composition of claim 1, wherein said additive is added to said lubricating oil composition before being used to lubricate a diesel engine.

6. The lubricating oil composition of claim 1, wherein said additive is added to said lubricating oil composition when being used to lubricate a diesel engine.

* * * * *